United States Patent
Filer et al.

(10) Patent No.: US 8,710,260 B2
(45) Date of Patent: Apr. 29, 2014

(54) PROCESS FOR PREPARING SUBSTITUTED AROMATIC CARBOXYLIC ACIDS

(75) Inventors: Crist N. Filer, Somerville, MA (US);
Terence P. Kelly, Norwell, MA (US);
Chrisopher Wright, Arlington, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 177 days.

(21) Appl. No.: 12/719,257

(22) Filed: Mar. 8, 2010

(65) Prior Publication Data

US 2010/0228048 A1    Sep. 9, 2010

Related U.S. Application Data

(60) Provisional application No. 61/158,005, filed on Mar. 6, 2009.

(51) Int. Cl.
*C07C 51/16*    (2006.01)
*C07C 51/255*    (2006.01)

(52) U.S. Cl.
USPC .......................................... 562/408

(58) Field of Classification Search
None
See application file for complete search history.

(56) References Cited

U.S. PATENT DOCUMENTS 4,880,894 A * 11/1989 Sunkel et al. ................. 548/152

OTHER PUBLICATIONS

Haglund et al. Synthesis, 1994, (3), 242-244.*
DiBiase et al. J. Org. Chem., 1980, (45), 3630-3634.*
Makosza et al. (Bull. Polish Acad. Sci. Chem., 1985, 33 (9-10), 427-32).*
Castedo et al. (Anales de Quimica, Serie C: Quimica Organica y Bioquimica, 1984, 80(2), 148).*
Buck et al, Stable Nitroaryl-lithium Compounds, Angew. Chem. Int. Ed. Engl., 1966, 1044, 5.
Warrener et al, An Improved Synthesis of 6-Methoxyanthranilic Acid, Austr. J. Chem., 1980, 2777-2779, 33.
Schmidt et al, Synthesis of Reference Substances for Highly Polar Metabolites of Nitroaromatic Compounds, Chemosphere, 1999, 3119-3130, 38.
Deady et al, A Convenient Procedure for Indirect Oxidation of Aromatic Methyl Groups to Aldehydes and Carboxylic Acids, Org. Prep. Proc. Int., 2003, 627-630, vol. 35 No. 6.
Kosuge et al, Synthesis of Nitro Compounds by Oxidation of Acylamino Compounds. VIII. Oxidation of Quinoline and its Derivatives., Pharm. Bull. 1954, 397-400, 2.
Haglund et al, Synthesis of 2-(2,6-Dinitrophenyl)malonates, -acetates and acetonitrile by Copper-Mediated Vicarious Nucleophilic Substitution, Synthesis, 1994, 242-243.

* cited by examiner

*Primary Examiner* — Johann R Richter
*Assistant Examiner* — Jennifer C Sawyer
(74) *Attorney, Agent, or Firm* — Gifford, Krass, Sprinkle, Anderson & Citkowski, P.C.; Weston R. Gould

(57) ABSTRACT

A process for preparing an aromatic carboxylic acid having a heteroatom containing substituent is provided that includes reaction in a vessel of an aromatic precursor having an aromatic core with at least one heteroatom containing substituent and at least one hydrogen extending from the core, with a haloacetonitrile under reaction conditions to form an aromatic acetonitrile with an acetonitrile moiety. The aromatic acetonitrile is exposed to an oxidizing agent under conditions to convert the acetonitrile moiety to a carboxylic acid group to prepare the aromatic carboxylic acid having the heteroatom containing substituent.

15 Claims, No Drawings

PROCESS FOR PREPARING SUBSTITUTED AROMATIC CARBOXYLIC ACIDS

CROSS-REFERENCE TO RELATED APPLICATIONS

This application claims priority of U.S. Provisional Patent Application Ser. No. 61/158,005 filed Mar. 6, 2009, which is incorporated herein by reference.

FIELD OF THE INVENTION

The present invention in general relates to a process for preparing substituted aromatic carboxylic acids and in particular to a process of oxidation of aromatic acetonitriles.

BACKGROUND OF THE INVENTION

The formation of aromatic carboxylic acids having a heteroatom containing substituent remains a complicated process. The reaction conditions needed to generate a carboxylate moiety are characterized by at least one problem of inducing undesired reaction of heteroatom substituted groups, mixed isomer formation, or resort to organometallic or heavy metal catalysts. As a result many substituted aromatic carboxylic acids produce waste streams of undesirable isomers and heavy metal waste.

By way of example, for the preparation of dinitrobenzoic acids, 2,6-dinitrobenzoic acid (2,6-DNBA) has been prepared by oxidation of 2,6-dinitrotoluene with acidic dichromate in moderate 58% yield (Austr. J. Chem. 1980, 33, 2777-2779). However, the use of chromium-containing oxidizing agent involves disposal of chromium-containing waste which is costly due to its toxicity. The use of less toxic but more expensive potassium permanganate produces 2,6-DNBA only in low yield (19%) (Chemosphere, 1999, 38, 3119-3130). 2,6-dinitrotoluene, which is described in these publications as a starting material, can be synthesized by direct nitration of toluene. However, the nitration results in mixtures of dinitrotoluene isomers, of which 2,6-dinitrotoluene is only a minor component, reducing significantly the overall yield of the target molecule. Deady et al. prepared 2,6-DNBA from 2,6-dinitrobenzyl bromide which was first oxidized to 2,6-dinitrobenzaldehyde in 40% yield using mercury(I) nitrate. The aldehyde obtained was then oxidized to 2,6-DNBA with aqueous permanganate in 65% yield (Org. Prep. Proc. Int. 2003, 65, 627-630). 2,6-dinitrobenzyl bromide used as the starting material was prepared from 2,6-dinitrotoluene by free radical bromination. Accordingly, the synthesis is rather complicated, and the use of highly toxic mercurates is needed. Buck et al. treated 2,6-dinitrobromobenzene with PhLi followed by carbonation to afford the target 2,6-DNBA in a reported 67% yield (Angew. Chem. Int. Ed. Engl., 1966, 5, 1044). However, 2,6-dinitrobromobenzene used as the starting material has to be prepared from benzene via multi-step low yielding approaches. Kosuge et al. have reported that 5-nitroquinoline can be oxidized to 2,6-DNBA with hydrogen peroxide in acetic acid in 23% yield (Pharm. Bull. 1954, 2, 397-400). Since the resinous substances formed made the isolation of 2,6-DNBA difficult, a further permanganate oxidation was needed to decompose the contaminants.

Other aromatic carboxylic acids containing heteroatom containing substituents that include amine or hydroxyl substituent of phenyl or conjugated aromatic ring systems also suffer these problems in synthetic preparation. Thus, there exists a need for a method to produce aromatic carboxylic acids having a heteroatom containing substituent operative at high yield.

SUMMARY OF THE INVENTION

A process for preparing an aromatic carboxylic acid having a heteroatom containing substituent is provided that includes reaction in a vessel of an aromatic precursor having an aromatic core with at least one heteroatom containing substituent and at least one hydrogen extending from the core, with a haloacetonitrile under reaction conditions to form an aromatic acetonitrile with an acetonitrile moiety. The aromatic acetonitrile is exposed to an oxidizing agent under conditions to convert the acetonitrile moiety to a carboxylic acid group to prepare the aromatic carboxylic acid having the heteroatom containing substituent.

DETAILED DESCRIPTION OF THE PREFERRED EMBODIMENTS

The present invention has utility as a method for preparing heteroatom substituted aromatic carboxylic acids from the heteroatom substituted aromatic precursor through reaction with haloacetonitrile under conditions sufficient to form heteroatom substituted aromatic carboxylic acid. Without intending to be bound by a particular theory, the inventive method involves a vicarious aromatic nucleophilic substitution (VNS) followed by oxidation. Preferably, these reactions are performed as a tandem, two-step procedure.

The inventive method is operative with both ortho-para and meta directing heteroatom containing substituents. Additionally, the inventive method is operative with a variety of aromatic and polyaromatic cores illustratively including phenyl, naphthyl, anthracyl, phenanthracyl, quinolinyl, and isoquinolinyl.

As used herein, a heteroatom containing substituent is defined as a moiety having an atom of nitrogen, sulfur, or ether oxygen bonded to the aromatic core.

An inventive method is summarized by the generic reaction

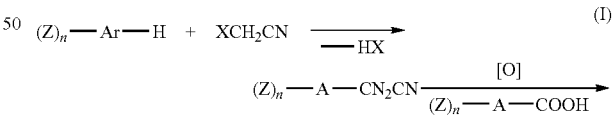

where Ar is an aromatic or polyaromatic core; Z is independently in each instance a heteroatom containing substituent of $-NO_2$, $-SO_3\text{-}M^+$, $-SO_3R$, or $-OR$; n is an integer value of between 1 and 4; X is Cl, Br or I; $M^+$ is $H^+$ or alkali metal cations; R is $C_1$-$C_6$ alkyl group, or a core Ar; and [O] denotes oxidizing conditions. It is appreciated that amine and hydroxyl substituents are vulnerable to undesired modification through reaction scheme (I). It is appreciated all substituents Z in (I) are either all the same or different and as such a precursor can, for example, simultaneously include only nitro, sulfonic acid, sulfonate-R substituents, or combinations thereof.

The reaction of a heteroatom containing substituent aromatic precursor $(Z)_n$-A—H with a haloacetonitrile $XCH_2CN$ is vicarious aromatic nucleophilic substitution (VNS) followed by oxidation. Typical reaction temperatures are between −35° C. and 30° C. and preferably between −25° C. and 10° C.

Representative heteroatom substituted aromatic precursors include nitrobenzenes such as nitrobenzene, 1,2-dinitrobenzene, 1,3-dinitrobenzene, 1,4-dinitrobenzene, and combinations thereof; and combinations thereof; benzene sulfonates such as benzene sulfonic acid, sodium benzene sulfonate; benzene disulfonates such as 1,2-benzene disulfonic acid, 1,3-benzene disulfonic acid, 1,4-benzene disulfonic acid, salts thereof, and combinations thereof.

Regardless of the specific precursor, scheme (I) proceeds through formation of an acetonitrile of the precursor. The positional preference of the acetonitrile on the aromatic core is appreciated to be largely dictated by the directing properties of the precursor heteroatom containing substituents under VNS reaction conditions. Generally, the substituents Z in scheme (I) tend to be meta position directors for phenyl cores and β directors in naphthyl core precursors according to the inventive process. The acetonitrile of the precursor is amenable to isolation and purification prior to oxidation to form the corresponding carboxylic acid.

Suitable exemplary oxidizing agents include Frémy's salt and TEMPO (2,2,6,6-tetramethylpiperidine-1-oxyl). The term "Frémy's salt" is used herein to define a nitrosodisulfonate salt, such as disodium nitrosodisulfonic acid ($Na_2NO(SO_3)_2$) or potassium nitrosodisulfonate (also known as potassium peroxylamine disulfonate). The oxidation step is optionally performed using Frémy's salt in the presence of a base, such as a carbonate, for example, sodium carbonate. The oxidation can be performed in a variety of suitable solvents, for example, acetonitrile, pyridine, and the like. The oxidation step is carried out at a variety of temperatures including ambient temperature of 20° C. The atmosphere for the oxidation step is ambient air, as well as inert atmospheres. While the reaction proceeds at ambient pressure of 760 torr, it is appreciated that reaction kinetics for both the formation of the acetonitrile of the precursor and the oxidation of the carboxylic acid are modified by adjusting the temperature-pressure reaction conditions.

The present invention is further detailed with respect to the following nonlimiting examples.

Example 1

Cuprous chloride (2.97 g, 30 mmol) is added to a goose neck additional funnel fitted to a 500 mL four neck round bottom flask with a rubber septum, thermometer, and magnetic stir bar. The flask is attached to a vacuum line and flame dried under vacuum. It is then allowed to cool to ambient temperature under argon. Potassium t-butoxide (42 mmol, 1M THF solution) is then added via syringe. The THF is carefully removed under vacuum to afford potassium t-butoxide as a white solid, and argon is reintroduced. Anhydrous dimethoxyethane (180 mL) is added via syringe, followed by the cuprous chloride (with stirring) in one portion, giving a dark mixture. Stirring is continued at ambient temperature for 45 min. Anhydrous pyridine (12 mL) is then added to the dark stirred mixture followed by 1,3-dinitrobenzene (2.02 g, 12 mmol) in 30 mL of anhydrous dimethoxyethane. After cooling the reaction to an internal temperature of −20° C., bromoacetonitrile (1.44 g, 12 mmol) in 30 mL of anhydrous dimethoxyethane is added via cannula with stirring over the course of 15 min. During the addition, the internal temperature is maintained at −20° C. and the reaction is stirred at this temperature for another 2 h and warms to ambient temperature for 30 min and then quenched with the addition of 60 mL of 3M HCl solution. The reaction mixture is then added to 600 mL of water and extracted with eight 50 mL portions of diethyl ether. The combined ether extracts are dried over sodium sulfate, filtered and evaporated to afford a dark oil of 2,6-dinitrophenyl acetonitrile whose $^1H$ NMR ($CDCl_3$) is in concert with the literature spectrum.

Example 2

Potassium nitrosodisulfonate (13.4 g, 50 mmol) in 500 mL of 4% aqueous sodium carbonate solution is added to a 1 L Erlenmeyer flask equipped with a large magnetic stir bar. Then, with stirring, a solution of 2,6-dinitrophenylacetonitrile (2.07 g, 10 mmol) in 50 mL of acetonitrile is gradually added over the course of 20 min at ambient temperature. Stirring continued for 3.5 h. Three separate sequential portions of additional potassium nitrosodisulfonate (2.6 g, 9.7 mmol) are added at time points 0.5 h, 1 h and 2 h, and stirred for 3.5 h in total. Diethyl ether (100 mL) is then added to the reaction and is stirred at ambient temperature for 1 h. The layers are separated and the ether layer is discarded. The aqueous layer is cautiously acidified with cone. HCl to pH 2, and 150 mL of diethyl ether is added to the mixture with stirring at ambient temperature for 0.5 h. The layers are separated and the aqueous layer is further extracted with 100 mL and 50 mL portions of diethyl ether. The combined ether layers are dried over magnesium sulfate, filtered and evaporated to afford 1.91 g (90% yield) of the 2,6-dinitrobenzoic acid.

Example 3

The process of Example 1 is repeated without addition of cuprous chloride or pyridine and a stirring reaction time of 6 h instead of 2 h with a comparable result.

Example 4

The product of Example 3 is reacted with Frémy's salt replaced in equimolar amount by TEMPO to yield 2,6-dinitrobenzoic acid in comparable yield.

Examples 5-12

The process of Examples 1 and 2 are repeated with equimolar substitution of the reagents and conditions, as detailed in Table 1, to afford substituted aromatic carboxylic acids. The reaction conditions unless noted otherwise are those detailed in the referenced examples.

TABLE 1

Reactions of Example 5

| Example | Heteroatom Substituted Aromatic Precursor | Precursor Amount (mmol) | t-BuOK Amount (mmol) | t-BuOCu Amount (mmol) | XCH₂CN X = Amount (mmol) | Major Product |
|---|---|---|---|---|---|---|
| 5 | 1,3-benzenedisulfonic acid (HO₃S–C₆H₄–SO₃H) | 12 | 12 | 30 | Br, 12 | 2,6-disulfobenzoic acid (COOH with HO₃S, SO₃H ortho) |
| 6 | 1,3-benzenedisulfonic acid | 12 | 24 | 30 | Br, 12 | 3,5-disulfobenzoic acid |
| 7 | ethyl benzenesulfonate (C₆H₅–SO₃CH₂CH₃) | 12 | 12 | 30 | Br, 12 | 2-(ethoxysulfonyl)benzoic acid |
| 8 | 1,3-dinitrobenzene | 12 | 24 | 30 | Br, 12 | 3,5-dinitrobenzoic acid |
| 9 | 1,4-dinitrobenzene | 12 | 12 | 0 | I, 12 | 2,5-dinitrobenzoic acid |
| 10 | 1-nitronaphthalene | 12 | 12 | 30 | Br, 12 | 8-nitro-2-naphthoic acid |
| 11 | 3-methoxyquinoline | 12 | 12 | 30 | Br, 12 | 3-methoxyquinoline-4-carboxylic acid |
| 12 | 3-ethoxy-8-sulfonatoisoquinoline (SO₃⁻Na⁺, OCH₂CH₃) | 12 | 12 | 30 | Br, 12 | 3-ethoxy-4-carboxy-8-sulfonatoisoquinoline |

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of preparing an aromatic carboxylic acid having a heteroatom containing substituent ortho, meta, or β of said carboxylic acid comprising:

reacting in a reaction vessel an aromatic precursor having an aromatic core having at least one heteroatom containing substituent and at least one hydrogen with a haloacetonitrile under reaction conditions to form an aromatic acetonitrile with an acetonitrile moiety and at least one heteroatom containing substituent, said heteroatom containing substituent ortho, meta, or β of said acetonitrile moiety;

exposing said aromatic acetonitrile having at least one heteroatom containing substituent to an oxidizing agent under conditions to convert the acetonitrile moiety into a carboxylic acid group to prepare said aromatic carboxylic acid having at least one heteroatom containing substituent ortho, meta, or β of said carboxylic acid.

2. The process of claim 1 wherein said aromatic acetonitrile is formed and the at least one heteroatom containing substituent is unchanged.

3. The process of claim 1 further comprising adding an alkoxide to the reaction vessel prior to the reacting step.

4. The process of claim 3 wherein the alkoxide is a tert-butyl oxide.

5. The process of claim 4 wherein the alkoxide comprises an alkali metal alkoxide.

6. The process of claim 5 wherein the alkali metal is present in equimolar or lower amount in the reaction vessel relative to the aromatic precursor.

7. The process of claim 5 wherein the alkoxide further comprises a transition metal alkoxide.

8. The process of claim 7 wherein the transition metal alkoxide is a copper alkoxide and further comprising a copper ligand.

9. The process of claim 3 wherein the alkoxide comprises:
a tert-butyl alkali metal alkoxide present in an equimolar or less amount relative to the aromatic precursor;
a copper tert-butyl oxide; and
a copper ligand.

10. The process of claim 1 wherein the aromatic precursor is a dinitro benzene.

11. The process of claim 1 wherein the aromatic core is phenyl, naphthyl, anthracyl, phenanthracyl, or quinolyl or isoquinolyl; and the at least one heteroatom containing substituent is two like heteroatom containing substituents.

12. The process of claim 11 wherein the two like heteroatom containing substituents are both nitro moieties.

13. The process of claim 1 wherein the at least one heteroatom containing substituent comprises at least one sulfonyl moiety.

14. A process of preparing an aromatic carboxylic acid having a heteroatom containing substituent comprising:
performing a two step reaction
wherein a first step comprises reacting $(Z)_n$—Ar—H with $XCH_2CN$ to produce $(Z)_n$—Ar—$CH_2CN$;
and
wherein a second step comprises reacting said $(Z)_n$—Ar—$CH_2CN$ under oxidizing conditions;
where Ar is an aromatic or polyaromatic core; Z is independently in each instance a heteroatom containing substituent of —$NO_2$, —$SO_3$-$M^+$, —$SO_3R$, or —OR; n is an integer value of between 1 and 4; X is Cl, Br or I; $M^+$ is $H^+$ or alkali metal cations; R is $C_1$-$C_6$ alkyl group, to form an aromatic carboxylic acid having a heteroatom containing substituent ortho, meta, or β of said acid.

15. The process of claim 14 wherein Ar is one of phenyl, naphthyl, anthracyl, phenanthracyl, quinolinyl, or isoquinolinyl.

* * * * *

UNITED STATES PATENT AND TRADEMARK OFFICE
CERTIFICATE OF CORRECTION

| | |
|---|---|
| PATENT NO. | : 8,710,260 B2 |
| APPLICATION NO. | : 12/719257 |
| DATED | : April 29, 2014 |
| INVENTOR(S) | : Crist N. Filer et al. |

It is certified that error appears in the above-identified patent and that said Letters Patent is hereby corrected as shown below:

Title page, item (75) under "Inventors," delete "Chrisopher" and insert --Christopher.--

Signed and Sealed this
Twenty-ninth Day of July, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,710,260 B2 | Page 1 of 1 |
| APPLICATION NO. | : 12/719257 | |
| DATED | : April 29, 2014 | |
| INVENTOR(S) | : Crist N. Filer et al. | |

It is certified that error appears in the above-identified patent and that said Letters Patent is hereby corrected as shown below:

<u>Title Page,</u>
Item [75], Inventors, "Christopher" (as corrected to read in the Certificate of Correction issued July 29, 2014) is deleted and patent is returned to its original state with third inventor name in patent to read --Crisopher--.

Signed and Sealed this
Thirtieth Day of September, 2014

Michelle K. Lee
*Deputy Director of the United States Patent and Trademark Office*